(12) United States Patent
Sinha et al.

(10) Patent No.: US 7,074,567 B2
(45) Date of Patent: Jul. 11, 2006

(54) ASSAY FOR HUMAN DNA FOR GENDER DETERMINATION

(75) Inventors: Sudhir K. Sinha, Metairie, LA (US); Dale J. Hedges, Baton Rouge, LA (US); Mark A. Batzer, Mandeville, LA (US)

(73) Assignees: Reliagene Technologies Inc., New Orleans, LA (US); Board of Supervisors Of Louisiana State University and Agricultural and Mechanical college, Baton Rouge, LA (US)

( * ) Notice: Subject to any disclaimer, the term of this patent is extended or adjusted under 35 U.S.C. 154(b) by 220 days.

(21) Appl. No.: 10/673,854

(22) Filed: Sep. 30, 2003

(65) Prior Publication Data

US 2005/0069903 A1    Mar. 31, 2005

(51) Int. Cl.
*C12Q 1/68* (2006.01)
*C12P 19/34* (2006.01)
*C07H 21/02* (2006.01)

(52) U.S. Cl. .......................... 435/6; 435/91.2; 536/23.1
(58) Field of Classification Search .................... 435/6, 435/91.2
See application file for complete search history.

(56) References Cited

U.S. PATENT DOCUMENTS 4,683,202 A    7/1987 Mullis 5,843,660 A * 12/1998 Schumm et al. ................ 435/6

OTHER PUBLICATIONS

White et al. ("Sexing of Human and Other Primate DNA" Biological Chemistry. Oct. 1998. vol. 379 pp. 1287-1288).*
Wang et al. ("Quantitation of mRNA by the polymerase chain reaction" Proc. Natl. Acad. Sci. Dec. 1989. vol. 86: pp. 9717-9721).*
Batzer et al. "Standardized Nomenclature for Alu Repeats" Journal of Molecular Evolution. 1996. 42: pp. 3-6).*
Wilson et al. ("Sexing of Human and Other Primate DNA" Biological Chemistry. Oct. 1998. vol. 379 pp. 1287-1288).*
Hedges et al., "*Mobile Element-Based Assay for Human Gender Determination,*" Analytical Biochemistry 312, pp. 77-79, 2003.

(Continued)

*Primary Examiner*—Kenneth R. Horlick
*Assistant Examiner*—Christopher M. Babic
(74) *Attorney, Agent, or Firm*—Robert E. Bushnell, Esq.

(57) ABSTRACT

A method for determining gender from a human DNA sample. The loci of Alu element insertion is selected, amplified and evaluated in terms of size of the fragment. The gender assay utilizes AluSTXa for the X chromosome, AluSTYa for the Y chromosome, or both AluSTXa and AluSTYa, to reduce the possibility of error to a negligible quantity. The inserted chromosome yields a large fragment when the homologous region is amplified. The males are distinguished as having two DNA amplicons present, while females have only a single amplicon. The kit adapted for carrying out the method includes a pair of primers to amplify the locus and optionally polymerase chain reaction regents.

14 Claims, 2 Drawing Sheets

OTHER PUBLICATIONS

Walker et al., "*Quantitative Intra-Short Interspersed Element PCR for Species-Specific DNA Identification,*" Analytical Biochemistry 316, pp. 259-269, 2003.

Walker et al., "*Human DNA Quantitation Using Alu Element-Based Polymerase Chain Reaction,*" Analytical Biochemistry 315, pp. 122-128, 2003.

Nicklas et al., "*Development of an Alu-Based, QSY 7-Labeled Primer PCR Method for Quantitation of Human DNA in Forensic Samples,*" J Forensic Science vol. 48, No. 2, pp. 282-291, Mar. 2003.

Nicklas et al., "*Development of an Alu-Based, Real-Time PCR Method for Quantitation of Human DNA in Forensic Sample,*" J Forensic Science vol. 48, No. 5, pp. 936-944, Sep. 2003.

Kass et al., "*Inter-Alu Polymerase Chain Reaction: Advancements and Applications*", Analytical Biochemistry vol. 288, pp. 185-193, 1995.

\* cited by examiner

ASSAY FOR HUMAN DNA FOR GENDER DETERMINATION

BACKGROUND OF THE INVENTION

1. Technical Field

The present invention concerns an assay for determination of gender from human DNA samples. More specifically, the invention concerns a process for determining gender by amplifying an inserted Alu sequence in a homologous X-Y region of human DNA using appropriate primers, and then determining the gender associated with the DNA by determining the length of the fragments; the invention also concerns compositions adapted for use with the process.

2. Description of the Related Art

DNA Typing

DNA (Deoxyribonucleic acid) typing is commonly used to identify the parentage of human children, and to identify the source of blood, saliva, semen, and other tissue found at a crime scene or other sites requiring identification of human remains. DNA typing involves the analysis of alleles of genomic DNA with characteristics of interest, commonly referred to as "markers." Most typing methods in use today are specifically designed to detect and analyze differences in the length and/or sequence of one or more regions of DNA markers known to appear in at least two different forms in a population. Such length and/or sequence variation is referred to as "polymorphism." Any region (i.e. "locus") of DNA in which such a variation occurs is referred to as a "polymorphic locus."

Genetic markers which are sufficiently polymorphic with respect to length or sequence have long been sought for use in identity applications, such as paternity testing and identification of tissue samples collected for forensic analysis. The discovery and development of such markers and methods for analyzing such markers have gone through several phases of development over the last several years.

By the early 1990s, the use of polymerase chain reaction (PCR) technology (disclosed in U.S. Pat. No. 4,683,202 (1987)) was combined with the analysis of loci. See K. Kasai et al., *Amplification of a Variable Number of Tandem Repeats* (VNTR) *Locus* (pMCT118) *by the Polymerase Chain Reaction* (PCR) *and Its Application to Forensic Science*, J. FORENSIC SCI. 35(5):1196–1200 (1990). The amplified products are separated through agarose or polyacrylamide gels and detected by incorporation of radioactivity during the amplification or by post-staining with silver or ethidium bromide. However, PCR can only be used to amplify relatively small DNA segments reliably, i.e. only reliably amplifying DNA segments under 3,000 bases in length. See M. Ponce et al., *PCR amplification of long DNA fragments*, NUCLEIC ACIDS RES. 20(3):623 (1992); R. Decorte et al., *Rapid Detection of Hypervariable Regions by the Polymerase Chain Reaction Technique*, DNA AND CELL BIOL. 9(6):461–469 (1990).

In recent years, the discovery and development of polymorphic short tandem repeats (STRs) as genetic markers has played an important role in DNA typing. In this approach, amplified alleles at each selected locus may be differentiated based on length variation. Amplification protocols with STR loci can be designed to produce small products, generally from 60 to 500 base pairs (bp) in length, and alleles from each locus are often contained within a range of less than 100 bp. This allows simultaneous electrophoretic analysis of several systems on the same gel or capillary electrophoresis by careful design of PCR primers such that all potential amplification products from an individual system do not overlap the range of alleles of other systems.

Gender Assays

Determination of gender from human DNA samples is a common problem in forensics laboratories and in prenatal gender determination. While several assays based on use of the polymerase chain reaction (PCR) are currently available for human sex typing, each of the current approaches has limitations.

Methods exist that are based on male-specific amplification, such as the amplification of the SRY locus. See A. H. Sinclair, et al., *A Gene from the Human Sex-Determining Region Encodes a Protein with Homology to a Conserved DNA-Binding Motif*, NATURE 346:240–244 (1990). These methods, however, lack an internal positive control to discriminate between female DNA and male DNA which has failed to amplify for technical reasons.

Restriction fragment length polymorphism (RFLP) assays can be based on sex-specific mutations at the ZFX/ZFY. See R. Reynolds, et al., *Gender Determination of Forensic Samples Using PCR Amplification of ZFX/ZFY Gene Sequences*, J. FORENSIC SCI. 41:279–286 (1996). RFLP assays, however, require a second enzyme digestion or hybridization step following the initial PCR amplification.

A recent method proposed by Cali, et al., INT. J. LEGAL MED. 116:133–138 (2002), is based on a single adenine insertion within a tandem repeat array at the DXYS156 locus. But this assay requires access to allele detection equipment potentially unavailable to forensics labs with limited resources.

A very widely used approach is based on the Amelogenin locus, which yields different sized PCR amplicons for the X and Y chromosome versions of the Amelogenin gene. See K. M. Sullivan, et al., *A rapid and quantitative DNA sex test: fluorescence-based PCR analysis of X-Y homologous gene amelogenin*, BIOTECHNIQUES 15:636–638, 640–631 (1993). However, this method misidentifies males as females in some cases (a frequency of 0.018% in Caucasian males, 1.85% among Indians, and as high as 8% in Sri-Lankans) due to a deletion in the AMEL Y region. See F. R. Santos, et al., *Reliability of DNA-Based Sex Tests*, NAT. GENET. 18:103 (1998); M. Steinlechner, et al., *Rare Failures in the Amelogenin Sex Test*, INT. J. LEGAL MED. 116:117–120 (2002); K. Thangaraj, et al., *Is the Amelogenin Gene Reliable for Gender Identification in Forensic Casework and Prenatal Diagnosis?*, INT. J. LEGAL MED. 116: 121–123 (2002). While the frequency of the deletion is relatively low, the crucial nature of forensic test results in circumstances such as rape and prenatal gender determination where there is risk for male-specific inherited disorders, makes any source of error a legitimate cause for concern. This has led several researchers to recommend that Amelogenin not be relied upon as the sole determinant of gender. See Santos, supra; Steinlechner, supra; Thangaraj, supra; B. Brinkmann, *Is the Amelogenin Sex Test Valid?*, INT. J. LEGAL MED. 116:63 (2002).

Alu Elements

Alu elements are transposable genetic elements which have amplified throughout primate evolution and now comprise roughly 10% of the human genome. Alu insertions are generally considered to be homoplasy-free with respect to human population genetics, as the probability of two Alu elements independently inserting in the same genomic location is extremely small. See M. A. Batzer, et al., *Alu Repeats and Human Genomic Diversity*, NAT. REV. GENET. 3:370–379 (2002).

SUMMARY OF THE INVENTION

Accordingly, it is an object of the present invention to provide a human gender assay that does not have the shortcomings or limitations of currently available assays.

It is another object of the present invention to provide an improved method for determining gender from a human DNA sample.

It is yet another object to provide a method for quantitation of DNA in the DNA sample.

It is also an object to provide an improved kit for gender determination.

In order to achieve the above and other objectives, the preferred embodiment of the present invention is that, for determining gender from a human DNA sample, the method includes the steps of providing a human DNA sample containing X chromosomal material and potentially containing Y chromosomal material, selecting at least one locus from a non-combining X-Y homologous region into which a monomorphic Alu element has been inserted during human evolution, amplifying the DNA sample in an amplification reaction, wherein the product of the reaction is a mixture of amplified alleles from the amplified locus present in the sample, and determining the gender of the DNA sample by evaluating the amplified alleles in terms of size and number.

The assays of the invention preferably utilize PCR amplification of a DNA sequence of a non-recombining X-Y homologous chromosomal region. Consequently, when this locus is amplified, the result is a larger amplicon associated with the respective X or Y chromosomal region into which the monomorphic Alu element has been inserted. Thus, relative amplicon size provides the reference for gender identification. The preferred embodiment of the gender assay utilizes AluSTXa for the X chromosome and AluSTYa for the Y chromosome. A more preferred embodiment utilizes both AluSTXa and AluSTYa, to reduce the possibility of error to a negligible quantity.

A kit for determining gender according to the above method comprises polymerase chain reaction regents which comprise a polymerase and buffer, and the pair of primers to amplify the locus.

The quantitation of DNA in the mixture sample can be achieved by analysis for products from the loci, for example, AluSTYa or AluSTXa. For example, the amount of male DNA in the unknown sample is computed by comparing the intensity of the signal from unknown samples with the intensity of standard male DNA or from the calibration curve, which can be generated from the results for the standard male DNA samples.

BRIEF DESCRIPTION OF DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION

The inventors determined on using the strategy of seeking an insertion of an Alu element into a non-recombining X-Y homologous region to create a means for differentiating between inserted and non-inserted chromosomes based on PCR amplicon size. While some recently integrated Alu insertions remain polymorphic in the human population, many ultimately reach fixation for the presence of the Alu insertion. Thus, the inventors hypothesized that locating fixed insertions on either the X or Y chromosome could provide a way of identifying the respective chromosome, as it was ascertained (see FIG. 1) that the inserted chromosome yields a larger fragment when the homologous region is amplified. The amplification is preferably by PCR although other amplification schemes are now being developed and can be used.

Figure 1:
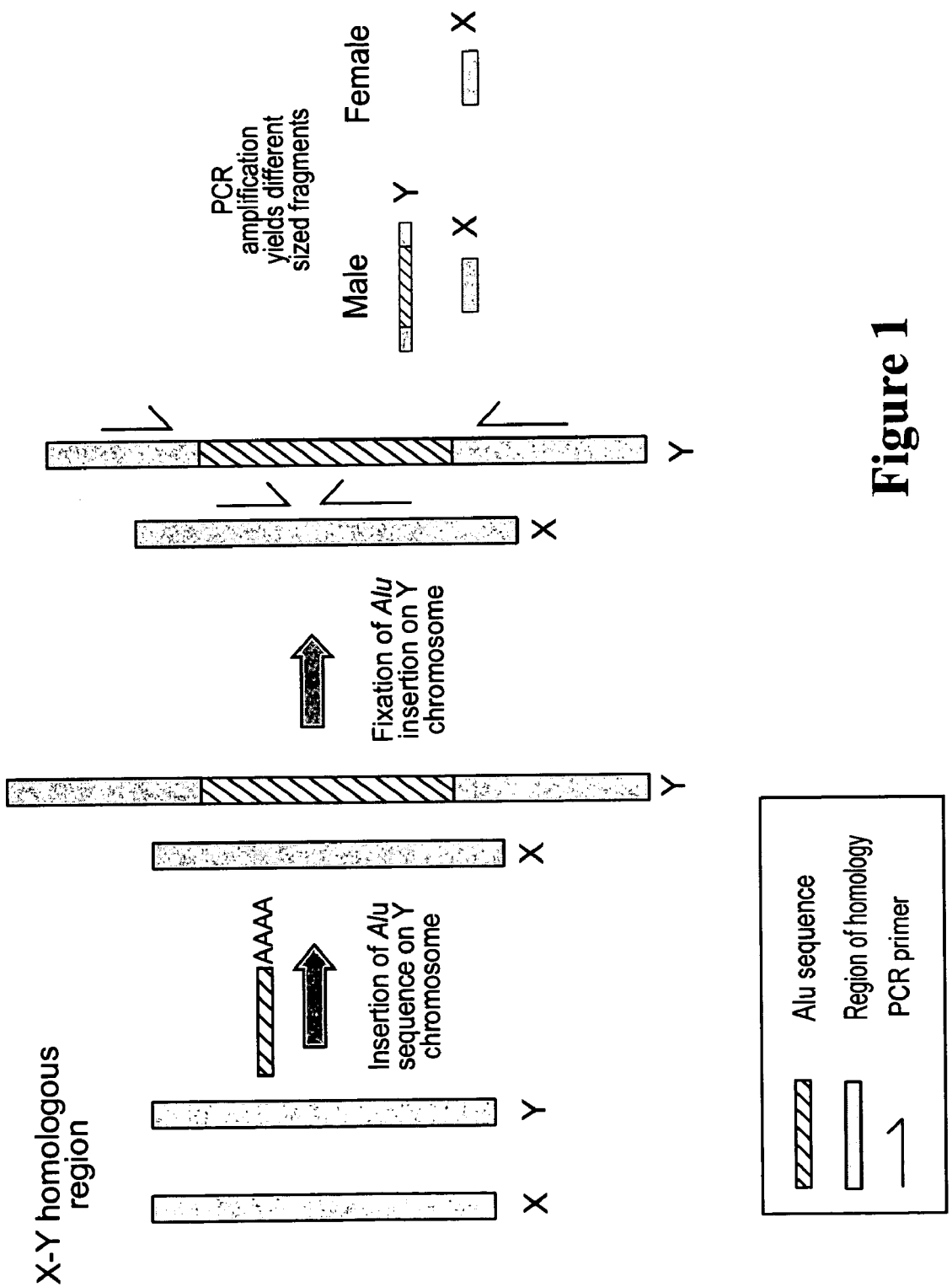
FIG. 1 is a diagram showing how PCR amplification yields different sized fragments for an inserted Alu sequence in a homologous X-Y region.

FIG. 1 is a schematic diagram of human sex-typing based upon the analysis of recently integrated Alu elements. In the diagram, an Alu insertion has occurred on the Y chromosome within an X-Y homologous region. Once fixed in the population, the Alu insertion sequence results in a larger amplicon on the Y chromosome, allowing for the differentiation of the sex chromosomes via PCR amplification. X chromosome-specific insertions function in the same manner.

By screening X-Y homologous Alu insertions for levels of insertion polymorphism, the inventors identified that two monomorphic Alu insertions meet the necessary criteria for a gender determination assay and are preferred. One is fixed on the X chromosome, AluSTXa, and one is fixed on the Y chromosome, AluSTYa. Both of the Alu elements presumably inserted and reached fixation in the human lineage prior to the radiation of modern humans from Africa. The inventors selected these loci for use in their gender assay.

The inventors then amplified DNA samples from 778 diverse (African-American, European-American, and Hispanic-American) individuals of defined sex from paternity/identity cases for both the AluSTYa and AluSTXa loci. The assays showed 100% accuracy in gender identification. The DNA samples used in the study consisted of 389 females (278 African-American, 102 European-American, and 9 Hispanic-American) and 389 males (288 African-American, 90 European-American, and 11 Hispanic-American). The statistical likelihood of 100% accuracy in gender identification of this large sample, on a random basis, is infinitesimal.

Figure 2:
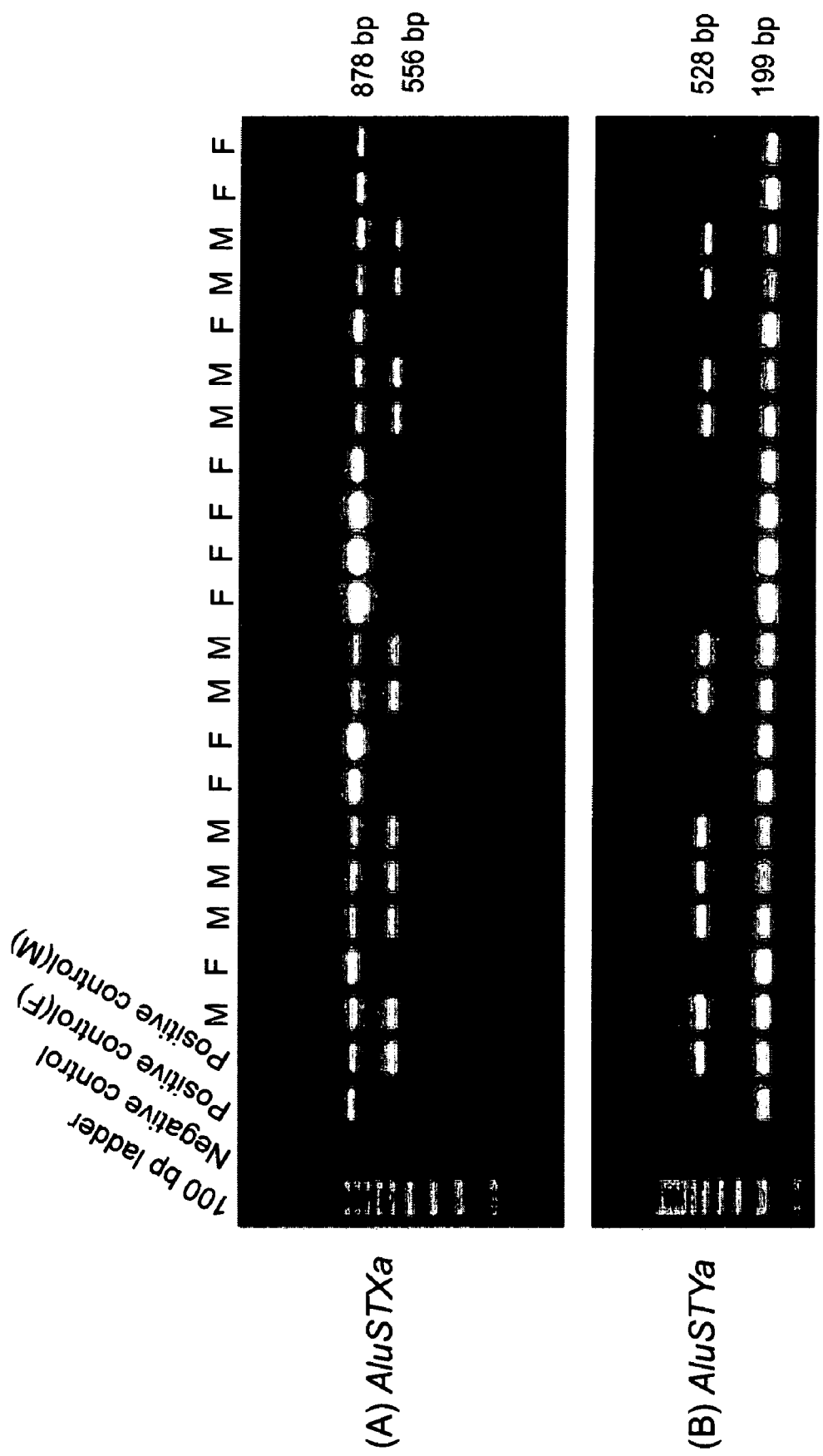
FIG. 2 shows resolution of fragments on gel after PCR amplification in accordance with the invention.

Amplification of the loci was conducted via a PCR reaction and fragments were resolved on a 2% agarose gel, as shown in FIG. 2. FIG. 2 is an agarose gel chromatograph that shows the results of the mobile element based sex typing assay. In FIG. 2, an agarose gel chromatograph from the analysis of twenty-four individuals using the genetic systems (a) AluSTXa and (b) AluSTYa is shown. Males are distinguished by the presence of two DNA fragments, while females have a single amplicon. F (female) and M (male) above each sample indicate the known gender. Individual PCR amplifications were performed in 25 µl (microliters) reactions using 25 ng of template DNA, 0.2 µM of each oligonucleotide primer, 200 mM deoxynucleotide-triphosphates, 1.5 mM MgCl2, 10 mM Tris-HCl (pH 8.4) and Taq® DNA polymerase (1 unit). Each sample was subjected to the same amplification cycle, as follows: initial denaturation of 150 seconds at 94° C., 32 cycles of one minute of denaturation at 94° C., one minute at the specific annealing temperature (58° C. for AluSTYa and 60° C. for AluSTXa), one minute of extension at 72° C., followed by a final extension at 72° C. for 10 minutes. For analysis, 20 μl of the PCR products was fractionated on a 2% agarose gel which contained 0.25 μg/ml of ethidium bromide. PCR products were visualized using ultra violet (UV) fluorescence.

The primers used for the Y insertion, AluSTYa, were

```
Forward
5'-CATGTATTTGATGGGGATAGAGG-3'    (SEQ ID NO:1)
and

Reverse
5'-CCTTTTCATCCAACTACCACTGA-3',   (SEQ ID NO:2)
``` yielding an Alu filled site (Y chromosome) fragment of 528 bp and an empty site (X chromosome) fragment of 199 bp. Primers for the X insertion, AluSTXa, were

```
Forward
5'-TGAAGAAATTCAGTTCATAGCTTGT-3'  (SEQ ID NO:3)
and

Reverse
5'-CAGGAGATCCTGAGATTATGTGG-3',   (SEQ ID NO:4)
``` yielding an inserted (X chromosome) fragment of 878 bp and an empty site (Y chromosome) fragment of 556 bp.

It will be apparent to those skilled in the art that some variations of these primers will also serve effectively, for example, adding or deleting one or a few bases from the primer and/or shifting the position of the primer by one or a few bases. Thus, equivalents of the foregoing primers, and thus primers encompassed by the present invention, include the primers specifically listed as well as modifications of these primers as described hereinabove.

For both of the selected loci, males are distinguished as having two DNA fragments present, while females only have a single fragment (see FIG. 2).

Combining these loci together for human gender identification provides an assay with increased accuracy for sex typing, since local deletions or other types of mutations that eliminate PCR would have to occur in at least two independent genomic locations to defeat the test. The speed and ease of agarose-based genotyping due to the ~300 bp difference between filled and empty alleles also enhances the utility of the assay in forensic laboratories.

This approach is also amenable to fluorescence-based amplicon detection, and quantitative PCR to resolve male and female contributions to sex-mixed samples. Furthermore, similar approaches based on ascertaining repetitive element insertions located in homologous sex chromosome regions will be useful for gender determination in other taxa of heterogametic sex. The invention is considered to extend generically to the use of other loci of X-Y homologous regions where the inserted chromosome yields a large fragment when the homologous region is amplified.

The quantitation of male DNA in the mixture sample can be achieved by analysis for products from the loci, for example, AluSTYa or AluSTXa. The amount of male DNA in the unknown sample is computed by comparing the intensity of the signal from unknown samples with the intensity of standard male DNA or from the calibration curve, which can be generated from the results for the standard male DNA samples.

Methods for Performing Assays

EXAMPLE 1

Stock primers were reconstituted in sterile TLE to a concentration of 100 μM. Then 1 ml of working solution of each primer at 2 μM was made by diluting 20 μl of each stock with 980 μl of TLE. This represents a 10× working concentration of each primer. PCR reagents were prepared on ice. 5 μl of DNA template (at 5 ng/μl) or controls was pipetted into each appropriate well. Then a master mix of all remaining PCR reagents was prepared. (See Table 1). 20 μl of master mix was pipetted into each well to make a final PCR reaction volume of 25 μl. PCR tubes or a plate were inserted into a thermal cycler.

TABLE 1

| Final concentration of PCR reagents: | | volume used (μl) | example for 20 samples |
|---|---|---|---|
| PCR buffer (10X) | 1X | 2.5 | 50 |
| Forward primer: | 0.2 μM | 2.5 | 50 |
| Reverse primer: | 0.2 μM | 2.5 | 50 |
| dNTPs: | 200 μM each | 0.2 | 4 |
| MgCl2: | 1.5 mM | 1.5 | 30 |
| Cresol red based dye (see supplies and solutions) | | 2.5 | 50 |
| Taq ® DNA polymerase: | 1 unit (i.e. 5 U/μl) | 0.2 | 4 |
| Sterile water: | balance to 20 μl reaction volume | | 162 |
| Final volume (20 μl × 20 samples) = | | | 400 |

PCR products were resolved by an agarose gel electrophoresis. 5 grams of agarose was placed in a bottle. 1×TBE (Tris/Boric acid/EDTA(ethylenediaminetetraacetic acid)) was added to a final volume of 250 ml (2%=2 g/100 ml). Agarose and TBE were swirled briefly. The bottle was placed in a microwave oven for approximately 3 minutes running time. The contents in the bottle were swirled once or twice as needed. When the agarose was completely in solution, the bottle was removed from the microwave oven. The contents in the bottle were cooled. 5 micro liters of ethidium bromide were added to 250 ml of agarose (final concentration 0.2 μg/ml). Then the ethidium bromide and agarose were swirled to be mixed. The agarose was cooled. The gel was slowly poured into a gel tray. Combs were added immediately after pouring gel. The gel was solidified for about 30 minutes. The gel tray was placed into an electrophoresis unit. The gel was covered with 1×TBE. About 20 micro liters of PCR product were loaded into each well. Electrophoresis was performed at 3.5 Volts/cm for at least 1 hour. DNA fragments were visualized under UV (ultraviolet) light.

EXAMPLE 2

Forensic Assay

The DNA from the source of blood, saliva, semen, and other tissues found at a crime scene was extracted by standard methods. The extracted DNA was then amplified for two regions AluSTXa and AluSTYa. The reaction mixture for the amplification for the AluSTXa region was comprised of 25 ng of template DNA, 0.2 μM of each oligonucleotide primer specific for AluSTXa region as here in described, 200 μM deoxynucleotide-triphosphates, 1.5 mM MgCl$_2$, 10 mM Tris-HCl (pH 8.4) and Taq®DNA polymerase (1 unit) in 25 μl volume and the amplification reaction was performed as follows: initial denaturation of 150 seconds at 94° C., 32 cycles of one minute of denaturation at 94° C., one minute at the 58° C., one minute of extension at 72° C., followed by a final extension at 72° C. for 10 minutes. Similarly, the reaction mixture for the amplification for the AluSTYa region was comprised of 25 ng of template DNA, 0.2 μM of each oligonucleotide primer specific for AluSTYa region, 200 μM deoxynucleotide-triphosphates, 1.5 mM $MgCl_2$, 10 mM Tris-HCl (pH 8.4) and Taq®DNA polymerase (1 unit) in 25 μl volume and the amplification reaction was performed as follows: initial denaturation of 150 seconds at 94° C., 32 cycles of one minute of denaturation at 94° C., one minute at the 60° C. (or 58° C. for AluSTYa), one minute of extension at 72° C., followed by a final extension at 72° C. for 10 minutes. The amplified products from these reactions were analyzed by electrophoresis; 20 μl of the PCR products was fractionated on a 2% agarose gel which contained 0.25 μg/ml of ethidium bromide. PCR products were visualized using ultra violet (UV) fluorescence. Males are distinguished by the presence of two DNA fragments, while females have a single amplicon.

EXAMPLE 3

Fluorescence-Based Assay

As previously indicated, the inventors' assay can be modified to embody fluorescence-based amplicon detection and quantitative PCR to resolve male and female contributions to sex-mixed samples.

The quantitation of male DNA in the mixture sample was performed by analysis for AluSTYa. A series of known male DNA samples (also called as standard) are amplified with the unknown sample containing the male DNA. The amount of male DNA in the unknown sample is computed by comparing the intensity of the signal from unknown samples with the intensity of standard male DNA. Alternatively, a calibration curve can be generated from the results for the standard male DNA samples. The quantity of the male DNA in the unknown sample was computed from the calibration curve.

Kits

It is considered that the scope of the invention extends to kits used to practice the assays of the invention. Thus, it is contemplated that the invention would be exploited by marketing kits for gender determination of unknown biological samples, using the principles and procedures described hereinabove. A human gender determination kit comprises reagents for a polymerase chain reaction, the primers for AluSTYa or AluSTXa, and optionally other reagents for polymerase chain reaction and/or detection.

EXAMPLE 4

Kit for Gender Determination

A kit suitable for performing a single gender determination assay comprises the following materials: a vial containing 500 ml of XYZ suspended in 5% aqueous NaCl solution; a vial containing 50 ml of Gender Determination Primer Mix (3 mg NaCl; 10 mg KBr; 14 ml $CH_3OH$; sufficient distilled water to bring mix up to 50 ml); a vial containing 10 ml of Reference Solution, and so on.

Several alternative methods for gender determination and quantitation using Alu insertions have been described above. While the invention has been described in connection with specific and preferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made. It should be appreciated that the scope of this invention is not limited to the detailed description of the invention hereinabove, which is intended merely to be illustrative, but rather comprehends the subject matter defined by the following claims.

---

What is claimed is:

1. A method for determining gender from a human DNA sample, said method comprising:
   providing a human DNA sample, said DNA sample containing X chromosomal material and potentially containing Y chromosomal material;
   amplifying at least one locus containing one of AluSTYa locus and AluSTXa locus of the DNA sample in an amplification reaction, wherein the product of the reaction is a mixture of amplified alleles from the amplified locus present in the sample; and
   determining the gender of the DNA sample by evaluating the amplified alleles in terms of size and number.

2. The method of claim 1, wherein said amplification reaction is a polymerase chain reaction.

3. The method of claim 2, wherein said at least one locus is AluSTYa locus.

4. The method of claim 3, wherein said amplification step comprises the step of using primer pairs containing the following sequences:

```
Forward
5'-CATGTATTTGATGGGGATAGAGG-3'    (SEQ ID NO:1)
and

Reverse
5'-CCTTTTCATCCAACTACCACTGA-3'.   (SEQ ID NO:2)
```

5. The method of claim 2, wherein said at least one locus is AluSTXa locus.

6. The method of claim 5, wherein said amplification step comprises the step of using primer pairs containing the following sequences:

```
Forward
5'-TGAAGAAATTCAGTTCATAGCTTGT-3'  (SEQ ID NO:3)
and

Reverse
5'-CAGGAGATCCTGAGATTATGTGG-3'.   (SEQ ID NO:4)
```

7. The method of claim 2, wherein said amplification step comprises an amplification of AluSTXa locus and an amplification of AluSTYa.

8. The method of claim 7, wherein said amplification step comprises the step of using primer pairs containing the following sequences: for said amplification of the AluSTXa locus,

```
5'-TGAAGAAATTCAGTTCATAGCTTGT-3'  (SEQ ID NO:3)
and

5'-CAGGAGATCCTGAGATTATGTGG-3';   (SEQ ID NO:4) and
``` for said amplification of the AluSTYa,

```
5'-CATGTATTTGATGGGGATAGAGG-3'    (SEQ ID NO:1)
and

5'-CCTTTTCATCCAACTACCACTGA-3'.   (SEQ ID NO:2)
```

9. The method of claim 2, wherein at least one primer of each pair has a fluorescent label covalently attached thereto.

10. The method of claim 1, wherein the sizes of the amplified alleles are evaluated by fragment resolution on an agarose gel.

11. The method of claim 10, wherein the sizes of the amplified alleles are evaluated by comparison with a size standard such that:
   for a Y insertion AluSTYa an Alu filled site for Y chromosome has size approximately 528 base pairs and an empty site for X chromosome has size approximately 199 base pairs; or
   for an X insertion AluSTXa an Alu filled site for X chromosome has size approximately 878 base pairs and an empty site for Y chromosome has size approximately 556 base pairs.

12. The method of claim 1, wherein male gender is characterized by presence of two DNA fragments and female gender is characterized by presence of one DNA fragment, for amplified loci.

13. A method for quantitating male DNA in a sample, said method comprising the steps of:
amplifying at least one locus of AluSTYa and AluSTXa in the sample by a polymerase chain reaction, wherein said locus is in a non-combining X-Y homologous region and contains a monomorphic Alu insertion;
detecting the product of the amplified locus; and
comparing the detected result with a result of standard male DNA to quantitate DNA in a sample.

14. The method of claim 13, wherein said amplification step comprises the step of using primer pairs containing at least one of the following pair of sequences:

5'-TGAAGAAATTCAGTTCATAGCTTGT-3' (SEQ ID NO:3) and
5'-CAGGAGATCCTGAGATTATGTGG-3'; (SEQ ID NO:4) and
5'-CATGTATTTGATGGGGATAGAGG-3' (SEQ ID NO:1) and
5'-CCTTTTCATCCAACTACCACTGA-3'. (SEQ ID NO:2)

* * * * *

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial
<220> FEATURE:
<223> OTHER INFORMATION: Primer for the Y insertion, AluSTYa

<400> SEQUENCE: 1
catgtatttg atggggatag agg                                            23

<210> SEQ ID NO 2
<211> LENGTH: 23
<212> TYPE: DNA
<213> ORGANISM: Artificial
<220> FEATURE:
<223> OTHER INFORMATION: Primer for the Y insertion, AluSTYa
```

-continued

```
<400> SEQUENCE: 2
ccttttcatc caactaccac tga                                                23

<210> SEQ ID NO 3
<211> LENGTH: 25
<212> TYPE: DNA
<213> ORGANISM: Artificial
<220> FEATURE:
<223> OTHER INFORMATION: Primer for the X insertion, AluSTXa

<400> SEQUENCE: 3
tgaagaaatt cagttcatag cttgt                                              25

<210> SEQ ID NO 4
<211> LENGTH: 23
<212> TYPE: DNA
<213> ORGANISM: Artificial
<220> FEATURE:
<223> OTHER INFORMATION: Primer for the X insertion, ALuSTXa

<400> SEQUENCE: 4
caggagatcc tgagattatg tgg                                                23
```